United States Patent
Smith

(10) Patent No.: US 11,293,858 B2
(45) Date of Patent: Apr. 5, 2022

(54) METHODS OF DISTINGUISHING HEMP FROM MARIJUANA

(71) Applicant: Big Sur Scientific, LLC, Aptos, CA (US)

(72) Inventor: Brian C. Smith, Aptos, CA (US)

(73) Assignee: Big Sur Scientific, LLC, Aptos, CA (US)

(*) Notice: Subject to any disclaimer, the term of this patent is extended or adjusted under 35 U.S.C. 154(b) by 0 days.

(21) Appl. No.: 17/381,318

(22) Filed: Jul. 21, 2021

(65) Prior Publication Data

US 2021/0381961 A1 Dec. 9, 2021

Related U.S. Application Data

(63) Continuation of application No. 17/341,954, filed on Jun. 8, 2021.

(60) Provisional application No. 63/036,182, filed on Jun. 8, 2020.

(51) Int. Cl.
| | |
|---|---|
| *G01N 21/3563* | (2014.01) |
| *G01N 33/00* | (2006.01) |
| *G01N 21/552* | (2014.01) |
| *G01N 21/84* | (2006.01) |

(52) U.S. Cl.
CPC ....... *G01N 21/3563* (2013.01); *G01N 21/552* (2013.01); *G01N 33/0098* (2013.01); *G01N 2021/8466* (2013.01); *G01N 2201/129* (2013.01)

(58) Field of Classification Search
CPC ............ G01N 21/3563; G01N 21/552; G01N 33/0098; G01N 2021/8466; G01N 2201/129
See application file for complete search history.

(56) References Cited

U.S. PATENT DOCUMENTS

| | | | |
|---|---|---|---|
| 3,487,223 A | 12/1969 | St. John | |
| 4,602,869 A | 7/1986 | Harrick | |
| 10,451,480 B2 | 10/2019 | Smith | |
| 2018/0143073 A1* | 5/2018 | Goldring | G01N 21/3563 |
| 2019/0033210 A1* | 1/2019 | Yarden | B07C 5/342 |

FOREIGN PATENT DOCUMENTS

WO WO-2018080938 A1 * 5/2018 ........... G01N 21/552

OTHER PUBLICATIONS

Giese, Matthew W. et al., "Method for the Analysis of Cannabinoids and Terpenes in Cannabis", *Journal of AOAC International*, vol. 98, No. 6, pp. 1503-1522 (Nov. 2015).
Lawson-Wood, Kathryn et al., "Comparison of Near- and Mid-Infrared Spectroscopy for Herb and Spice Authenticity Analysis", PerkinElmer Inc., Waltham, MA (2016).

(Continued)

*Primary Examiner* — Dominic J Bologna
(74) *Attorney, Agent, or Firm* — Smith Patent, LLC; Chalin A. Smith

(57) ABSTRACT

Systems and methods to measure Total THC easily and accurately in cannabis plant material to discriminate between legal hemp and illegal marijuana. In a particularly preferred embodiment, infrared spectral measurements are made of samples, a plurality of calibration models are applied, and a given sample is classified as to whether it is hemp or marijuana.

7 Claims, 6 Drawing Sheets

(56) References Cited

OTHER PUBLICATIONS

Neumann, Norbert et al., "Tunable Infrared Detector with Integrated Micromachined Fabry-Perot Filter", *J. Micro/Nanolith. MEMS MOEMS*, vol. 7, No. 2, pp. 021004-1-021004-9 (Apr. 2008).

Smith, Brian C. et al., "Optimization of Cannabis Grows Using Fourier Transform Mid-Infrared Spectroscopy," PerkinElmer Inc., Waltham, MA (2016).

Smith, Brian C, "Spectroscopy Versus Chromatography for Potency Analysis", *Cannabis Science and Technology*, vol. 2, No. 6, pp. 10-14 (Nov./Dec. 2019).

Smith, Brian C. et al., "Distinguishing Hemp from Marijuana by Mid-Infrared Spectroscopy", *Cannabis Science and Technology*, vol. 3, No. 6, pp. 24-38 (Jul./Aug. 2020).

Smith, Brian C, "A Proposed Representative Sampling Plan for Hemp Grows", *Cannabis Science and Technology*, vol. 3, No. 6, pp. 10-13 (Jul./Aug. 2020).

Smith, Brian C., "Hemp Testing Insanity III: This Time It's the USDA!", *Cannabis Science and Technology*, vol. 4, No. 2, pp. 10-13 (Mar. 2021).

Sun, Lan et al., "Pharmaceutical Raw Material Identification Using Miniature Near-Infrared (MicroNIR) Spectroscopy and Supervised Pattern Recognition Using Support Vector Machine", *Applied Spectroscopy*, vol. 70, No. 5, pp. 816-825 (2016).

\* cited by examiner

METHODS OF DISTINGUISHING HEMP FROM MARIJUANA

PRIORITY

This application is a continuation of U.S. patent application Ser. No. 17/341,954 filed Jun. 8, 2021, which, in turn, claims the benefit of and priority to U.S. Prov. Appl. No. 63/036,182, filed on Jun. 8, 2020, entitled "Systems and Methods for Distinguishing Hemp from Marijuana". Each disclosure is its entirety is incorporated by reference herein.

TECHNICAL FIELD OF THE PRESENT INVENTION

Embodiments relate generally to testing to discriminate between legal hemp and illegal marijuana, and more specifically to the measurement of total THC in samples using infrared spectral measurements and a plurality of calibration models.

BACKGROUND OF THE PRESENT INVENTION

The 2018 United States Farm Bill as passed by the United States Congress and a subsequent Interim Final Rule as promulgated by the United States Department of Agriculture (USDA) on Oct. 29, 2019 make it legal to grow and possess cannabis plant material in the United States so long as the Total THC content by dry weight does not exceed 0.3%. Since passage of the Farm Bill, legal hemp shipments have been seized by law enforcement around the country under the mistaken assumption the material was illegal marijuana. Places where this has happened include Idaho, Oklahoma, New York City, Texas, and Colorado. As a result of these seizures innocent people have spent time in jail, thousands of dollars of valuable hemp have been seized, bad press for law enforcement has ensued, and lawsuits have been filed. Another outcome of the new law is that forensic labs are being swamped with cannabis plant material samples, many of which are legal hemp, tying up resources and spending money that is better spent on other cases. The law and interim final rule require state departments of agriculture to develop programs for cannabis plant material testing. The interim final rule says that at least one cutting per acre of cannabis plant material should be tested. This means come harvest season each state must test thousands of samples during a short period of time. Many states will not have the capacity to perform the Federally required amount of testing properly.

Since Federal law clearly states that there is a 0.3% threshold for legality, any method used to distinguish hemp from marijuana must produce a weight percent Total THC value. When thinking about a chemical analysis method to measure concentrations, four criteria can be used: accuracy, cost, time, and the ability to perform representative sampling. This is illustrated in FIG. 1 as the Golden Rectangle of Chemical Analysis.

Gas and liquid chromatography can be used to measure Total THC in cannabis plant material. However, chromatography is slow as it can take 20 minutes or more to prepare and analyze a sample. Chromatography is also expensive. Instruments cost tens of thousands of dollars, and there are expensive consumables including vials, filters, syringes, columns, and solvent. There is also the cost of legal solvent disposal and required safety equipment such as fume hoods, lab coats, gloves, and safety goggles. Another component is labor. Chromatographic systems are complex and difficult to use and require degreed and highly trained scientists to operate, who are more expensive to employ than laypeople.

Cannabis plant material is inhomogeneous, and to minimize sampling error representative sampling must be performed. This means that many samples need to be analyzed and the results averaged to correctly characterize a lot of cannabis plant material and minimize sampling error. Thus, for an analytical method to be practical for representative sampling it must be fast, easy, and inexpensive. Chromatography fails here because it is slow, expensive, and difficult to use.

For law enforcement and state departments of agriculture to distinguish hemp from marijuana in the field they will need a system that is portable in addition to the criteria listed in FIG. 1. Since chromatography involves the use of heavy equipment that needs a power supply, requires a fume hood, solvents, and other consumables, and is difficult to use it is not practical for field use, particularly by laypeople.

There is a need then for law enforcement to analyze seized cannabis plant material in the field to prevent false arrests, for forensic labs to weed out non-prosecutable cases to help streamline their operations, and for state departments of agriculture to increase their testing capacity to comply with the law. Any method for this purpose needs to be accurate, fast, inexpensive, easy to use, portable, and capable of representative sampling.

SUMMARY OF THE PRESENT INVENTION

The present invention addresses the afore-noted needs in the art by providing a method for classifying dried, ground cannabis plant material samples and thereby distinguishing marijuana from hemp. More particularly, the present invention utilizes infrared spectrometry methods and calibration models to (a) determine a total THC value for a sample of cannabis plant material and (b) classify the sample as high Total THC cannabis or low Total THC cannabis. In particularly preferred embodiments, samples designated as low Total THC cannabis are further subjected to a second Total THC calibration model to determine a second Total THC value, and evaluating said second Total THC value against a second Total THC threshold.

In preferred embodiments, the spectral region of the infrared spectrum or spectra may be chosen from among near infrared, mid-infrared, and far infrared; the infrared spectrometer type may be chosen from among grating, Fourier transform, filter, tunable filter, and Fabry-Perot interferometer; and the infrared sample analysis method may be chosen from among reflectance, specular reflectance, diffuse reflectance, internal reflectance, external reflectance, attenuated total reflectance, frustrated total internal reflectance, KBr pellets, mulls, cast films, and heat and pressure films.

The present invention contemplates the use of calibration models to correlate measured spectra to Total THC value, more particularly first and second THC calibration models selected from among Beer's Law, Classical Least Squares, K-Matrix, Inverse Least Squares, P-Matrix, Principal Components Analysis, Principal Components Regression, Partial Least Squares, Neural Networks, Support Vector Machine, and ANOVA. Using such automated processes, it is an objective of the present invention to enable the rapid and reliable differentiation of controlled substances (e.g., marijuana) from permitted commercial materials (e.g., hemp).

These and other objects and features of the invention will become more fully apparent when the following detailed description is read in conjunction with the accompanying figures and examples. However, it is to be understood that both the foregoing summary of the invention and the following detailed description are of a preferred embodiment, and not restrictive of the invention or other alternate embodiments of the invention. In particular, while the invention is described herein with reference to a number of specific embodiments, it will be appreciated that the description is illustrative of the invention and is not constructed as limiting of the invention. Various modifications and applications may occur to those who are skilled in the art, without departing from the spirit and the scope of the invention, as described by the appended claims.

BRIEF DESCRIPTION OF THE FIGURES

Various aspects and applications of the present invention will become apparent to the skilled artisan upon consideration of the brief description of figures and the detailed description of the present invention and its preferred embodiments that follows.

DETAILED DESCRIPTION OF THE PREFERRED EMBODIMENTS

Figure 1:
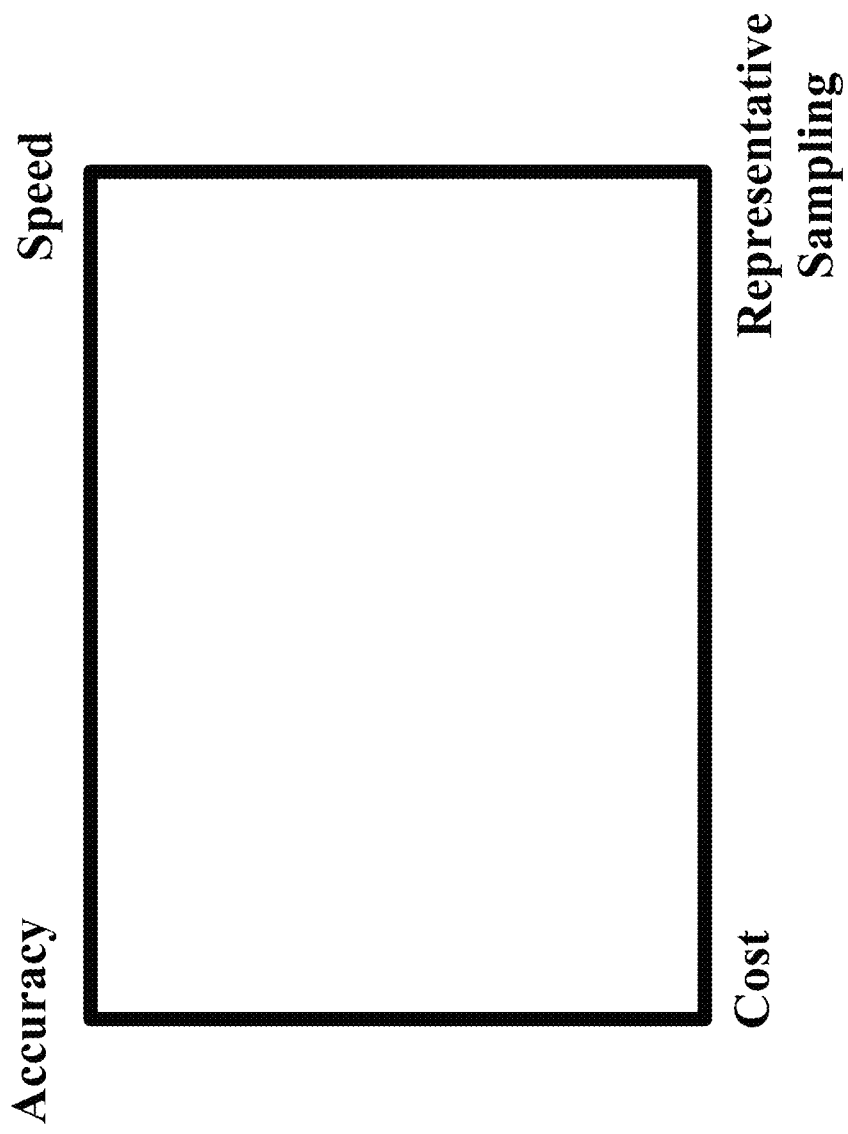
FIG. 1 The Golden Rectangle of Chemical analysis. The criteria that should be used to evaluate chemical analysis methods are accuracy, speed, cost, and the ability to perform representative sampling.

Before the present materials and methods are described, it is to be understood that this invention is not limited to the specific devices, systems, methodologies or protocols described hereinbelow, as these may vary in accordance with routine experimentation and optimization. It is also to be understood that the terminology used in the description is for the purpose of describing the particular versions or embodiments only, and is not intended to limit the scope of the present invention which will be limited only by the appended claims. Accordingly, unless otherwise defined, all technical and scientific terms used herein have the same meaning as commonly understood by one of ordinary skill in the art to which the present invention belongs. However, in case of conflict, the present specification, including definitions below, will control.

Terms and Definitions

The words "a", "an" and "the" as used herein mean "at least one" unless otherwise specifically indicated.

For the purposes of this patent application these terms will have the following meanings:

Percent, Weight %, Wt. %, and % —the weight percent of an analyte in a sample.

Cannabis—Plants of genus cannabis including but not limited to the species Cannabis Sativa, Cannabis Indica, and Cannabis Ruderalis.

Cannabis Plant Material—the dried, ground parts of the genus Cannabis plant including but not limited to buds, flowers, stems, stalks, leaves, and seeds.

THCA—Tetrahydrocannabinolic Acid

THC—Δ-9 Tetrahydrocannabinol

Total THC—=0.877(THCA)+THC

First Total THC Value—a Total THC wt. % value obtained from application of a first calibration model to an infrared spectrum.

First Total THC Threshold—Samples at or below this value are classified as low Total THC cannabis, whereas samples above this value are classified as high Total THC cannabis or in other words marijuana. In one embodiment the value of the first Total THC threshold is 5%

Second Total THC Value—a Total THC wt. % value obtained from application of a second calibration model to an infrared spectrum.

Second Total THC Threshold—Samples at or below this value are classified as hemp, whereas samples above this value are classified as marijuana. In one embodiment the second Total THC threshold is 0.3%.

High THC Cannabis—Cannabis plant material containing more than a first Total THC threshold by dry weight.

Low THC Cannabis—Cannabis plant material containing less than a first Total THC threshold by dry weight.

Marijuana—Cannabis plant material containing more than 0.3% Total THC.

Hemp—Cannabis plant material containing 0.3% or less Total THC

Spectroscopy—the study of the interaction of light with matter. The measurements obtained by spectroscopy are typically called spectra or a spectrum. Measuring a spectrum typically comprises examining a sample of material with electromagnetic radiation (EMR), and then plotting the measured intensity of said EMR after it has interacted with the sample versus some property of the EMR. Examples of EMR properties that can be plotted in a spectrum include but are not limited to frequency, wavelength, and wavenumber. Examples of EMR intensity that can be plotted in spectra include but are not limited to arbitrary units, transmittance, percent transmittance, absorbance, Kubelka-Munk units, reflectance, Log reflectance, emission, scattering intensity, and emittance. Examples of EMR that can be used to measure spectra include but are not limited to radio waves, microwaves, far infrared, mid-infrared, near infrared, ultraviolet, visible, and x-rays.

Infrared—EMR from 14,000 to 10 cm−1.

Mid-infrared—EMR from 4000 to 400 cm−1.

Near Infrared—EMR from 14,000 to 4000 cm−1.

Far Infrared—EMR from 400 to 10 cm−1.

Spectrum—A plot of a measure of light intensity versus some property of light.

Spectrometer—an instrument that measures a spectrum.

Calibration Model—A mathematical representation that relates one set of data to another.

Algorithm—A mathematical system, method, or construct for performing calculations, generating data, or making decisions.

Decision Point—The spot in a classification where a decision as to how to proceed is made based on measured data or results.

Hierarchical Method—The stepwise implementation of a method with multiple steps and decision points to achieve an outcome.

Classification—The act of sorting things into categories.

Category—A general or comprehensive division; a class.

Percent Successfully Classified—The percentage of a set of samples properly classified by a method.

Quantitative Infrared Spectroscopy:

Infrared spectroscopy is the study of the interaction of infrared light, otherwise known as heat, with matter. Different infrared wavelength regions can be used to analyze samples including the near infrared (NIR) and the mid-infrared (MIR). NIR wavelengths are shorter than MIR wavelengths. Infrared spectroscopy is used to determine analytes in agricultural crops including hay, forage, and grain, and is used throughout the food, forensic, pharma, and many other industries. Infrared spectroscopy is used for the purpose of distinguishing hemp from marijuana because it can give accuracy equivalent to chromatography, is fast as it often takes only 2 minutes total to analyze a sample, requires no weighing, extracting, filtering, or diluting so it is low cost per analysis, and given it is fast, easy, and inexpensive lends itself well to representative sampling and can feature push button operation so anyone can use it. Also, these instruments may be made portable.

Quantitative spectroscopic measurements make use of Beer's Law which states that $$A = \varepsilon l c$$

where: A=Absorbance
  $\varepsilon$=absorptivity
  l=pathlength
  c=concentration.

The amount of light absorbed by a sample, A, can be measured by a spectrometer. The absorptivity is a constant for a given molecule absorbing at a specific wavelength. It also is the proportionality constant between Absorbance and concentration. The pathlength, l, is the thickness of sample seen by an EMR beam. In the present invention this variable is fixed thanks to the use of the Attenuated Total Reflectance sampling technique. C is the concentration of analyte in the sample.

Although methods and materials similar or equivalent to those described herein can be used in the practice or testing of embodiments of the present invention, the preferred methods, devices, and materials are depicted in the accompanying figures and described hereinafter. However, the embodiments described herein are merely intended to illustrate the principles of the invention. Those skilled in the art will recognize that variations and modifications may be made to the embodiments without changing the principles of the invention herein disclosed. Accordingly, the accompanying figures, described in detail below that depict aspects of the invention are in no way intended to limit the scope of the present invention.

EXAMPLES

Illustrative Embodiments

The current invention relates to systems and methods for distinguishing between hemp and marijuana by measuring total THC using infrared spectral measurements and a plurality of calibration models. In one embodiment, infrared spectral measurements of a sample and the application of a plurality of calibration models gives the ability to distinguish hemp from marijuana with 95+% accuracy in a unit that features push button operation so anyone can use it, a two-minute analysis time, low cost per analysis, the ability to analyze many samples quickly and easily to allow proper representative sampling, and portability so it can be used in the field or roadside by law enforcement officers.

Figure 2:
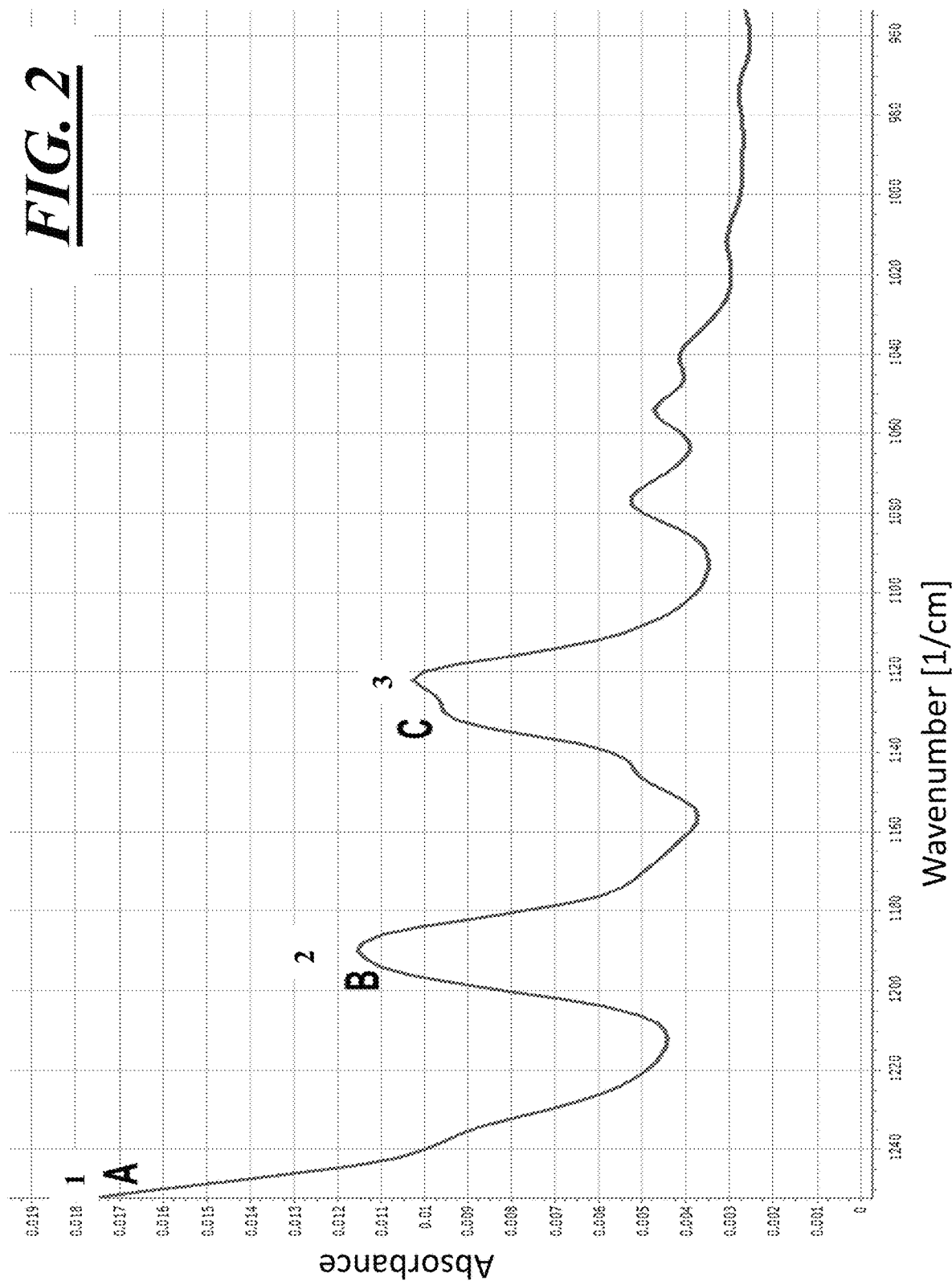
FIG. 2 The infrared spectrum of pure THCA from 1250 to 960 cm−1

Previous work has shown that in cannabis plant material much of the contribution to the Total THC value is from THCA. The infrared spectrum of pure THCA from 1250 to 960 cm−1 is shown in FIG. 2. The peak labeled 1 is the shoulder of a larger peak centered at 1256 cm−1, 2 is at 1190 cm−1, and 3 is at 1120 cm−1.

In going from hemp with low Total THC values to recreational marijuana with high Total THC values, for quantitation to be possible, there should be infrared spectral features whose size changes with Total THC content. This is seen in FIG. 3.

Figure 3:
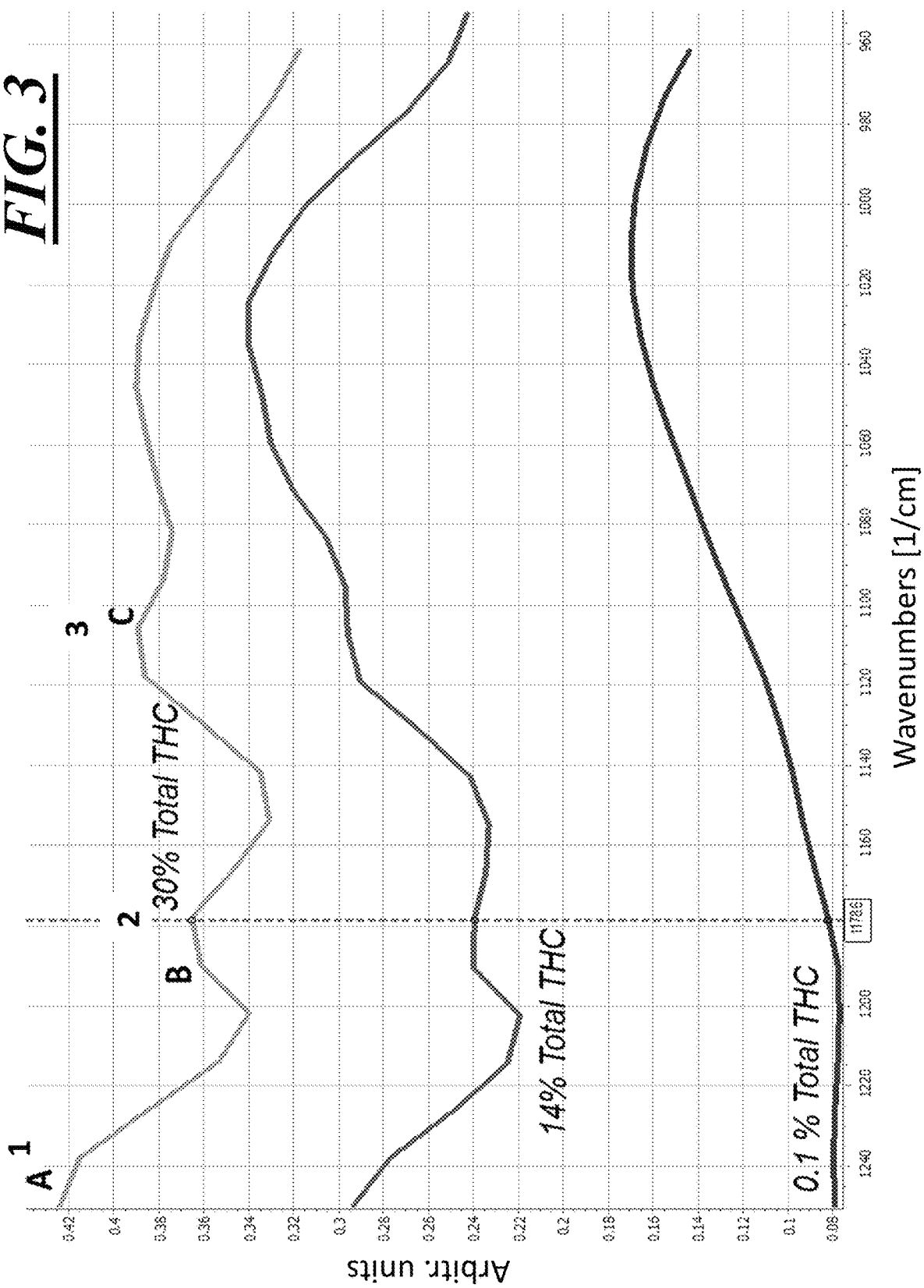
FIG. 3 Mid-infrared spectra of three cannabis plant samples containing varying amounts of Total THC. Bottom: 0.1% Total THC. Middle: 14% Total THC. Top: 30% Total THC.

The same infrared features present in the spectrum of pure THCA as seen in FIG. 2 are clearly seen in the spectra of cannabis plant material in FIG. 3, and are labeled 1, 2, and 3 respectively. Note that as the Total THC content goes from 0.1%, to 14%, to 30% in FIG. 3, the mid-infrared features clearly get larger. This correlation between peak size and Total THC value means Beer's Law can be used as the basis to use infrared spectroscopy to quantitate Total THC in cannabis plant material.

The literature teaches that a single calibration model should be used to analyze samples. The Total THC value in cannabis plant material can vary from 0.1% to over 30%. Based on literature teaching, a single Total THC concentration spanning this range should be used. However, it is found that this calibration is not accurate enough to reliably distinguish hemp from marijuana. It is known that calibration accuracy depends upon, amongst other things, the number of calibration data points, the concentration range they span, and their structure. Again, the required level of accuracy with a single calibration is not achieved. A solution is to go against literature teaching and take a multi-step approach to the problem. A flowchart of the method of the present invention is seen in FIG. 4.

Figure 4:
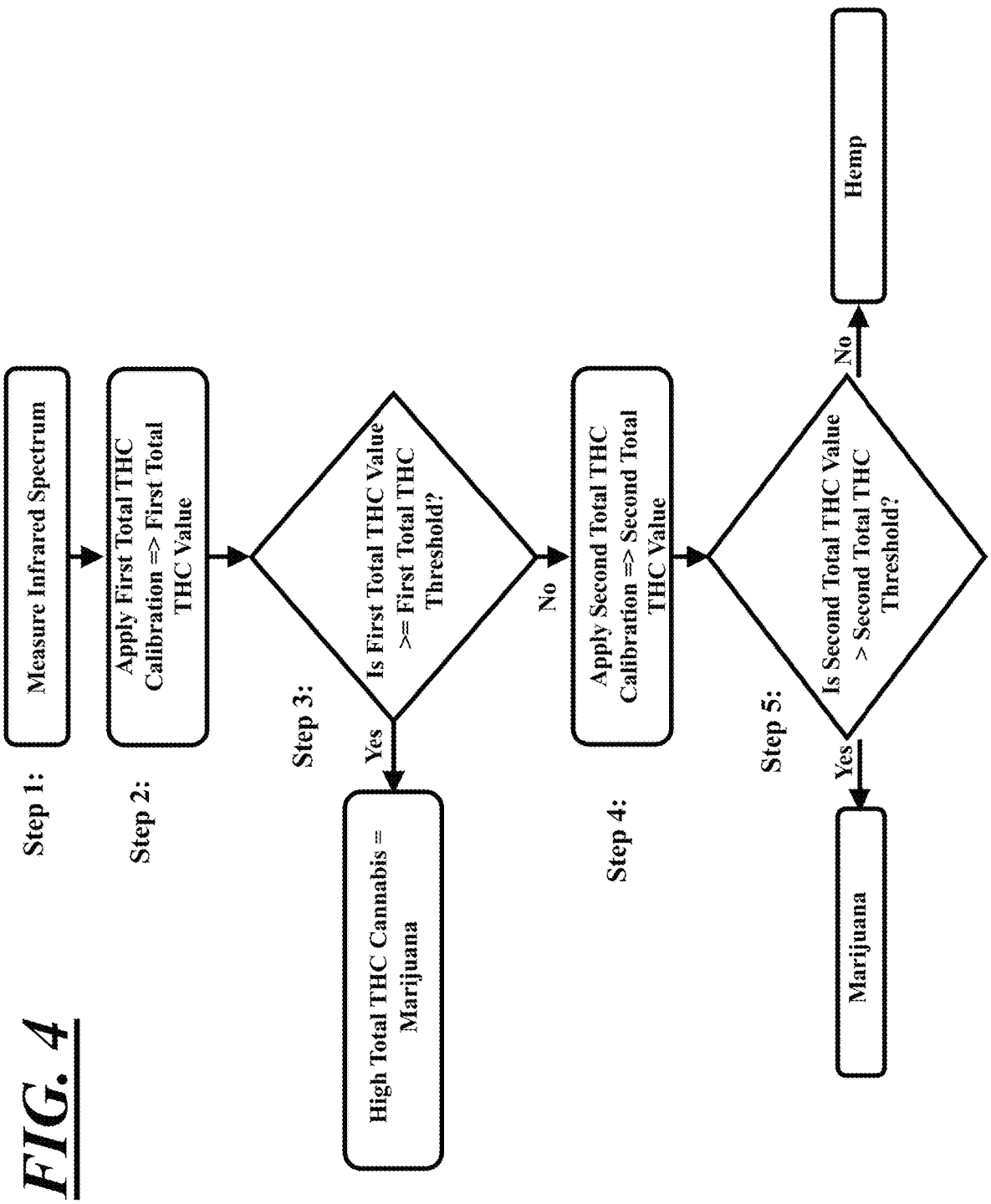
FIG. 4 A flow chart of the Total THC Classification method for cannabis plant material classification.

In one embodiment illustrated in FIG. 4, the infrared spectrum of a dried, ground cannabis plant sample is measured, Step 1, and a first Total THC calibration, in one embodiment a global calibration spanning a broad concentration range, is applied to the spectrum to give a first Total THC value, Step 2. The first Total THC value is compared to a first Total THC threshold, Step 3, which in one embodiment is 5%. If the first Total THC value is equal to or greater than the first Total THC threshold the material is classified as high total THC cannabis, that is marijuana, and no further analysis is needed. However, when the first Total THC value is less than the first Total THC threshold, it may be hemp or marijuana, and a broad range Total THC calibration is not accurate enough to determine whether the sample's Total THC level is above or below the 0.3% legal limit. In this case a second Total THC calibration is applied to the sample's infrared spectrum to give a second Total THC value, Step 4. Said second Total THC calibration will typically contain many data points at low concentration to enhance accuracy. The second Total THC value is compared to a second Total THC threshold, Step 5. In one embodiment this threshold is the 0.3% Total THC legal limit. In this case samples that are at or below the second Total THC threshold are legally hemp, and samples above the second Total THC threshold are marijuana.

Figure 5:
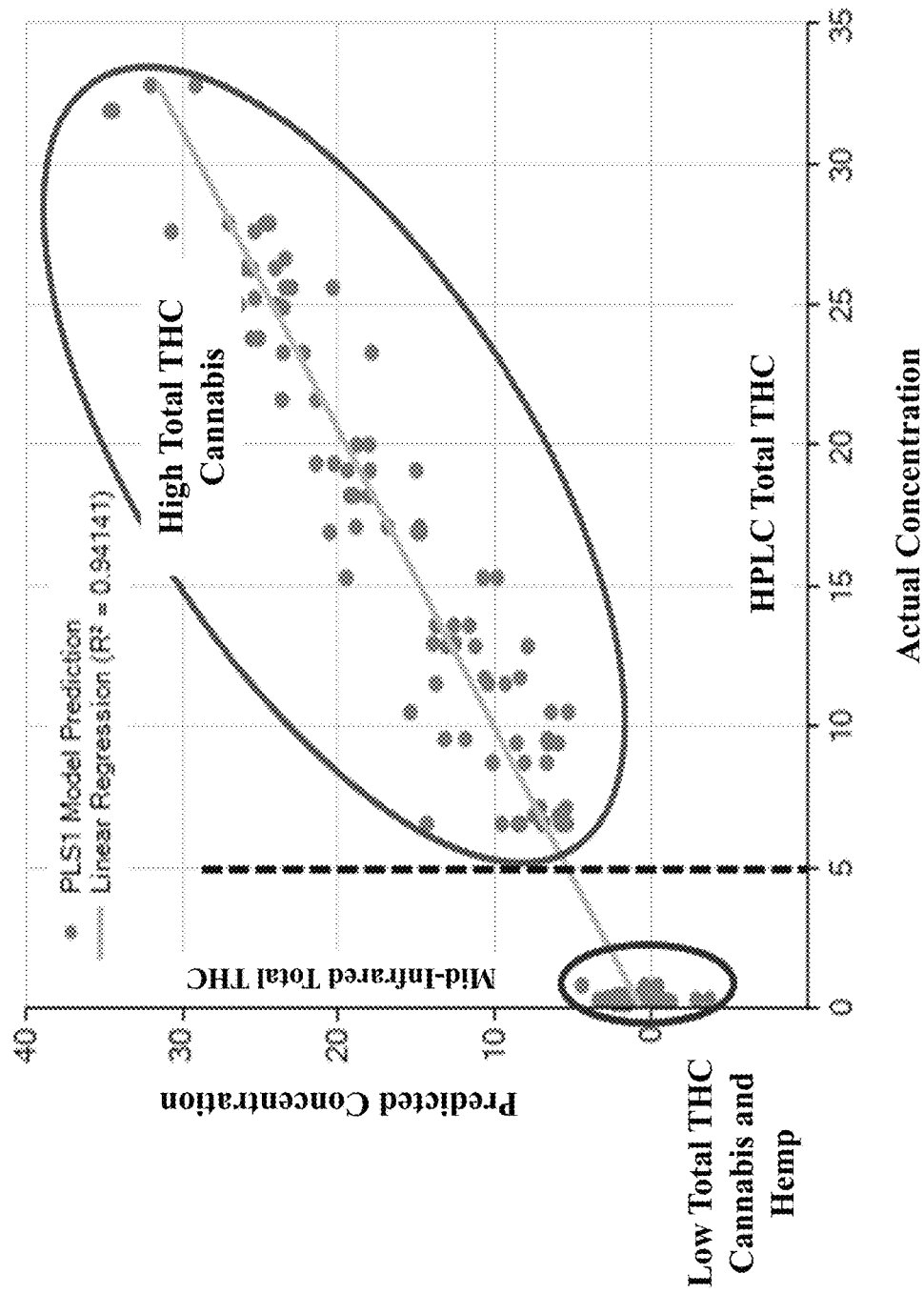
FIG. 5 The correlation chart for a global Total THC calibration. Total THC values as measured by HPLC are on the x-axis, and Total THC values as measured by infrared spectroscopy are on the y-axis. This data set contains 129 calibration data points. Total THC values ranged from 0.1% to 33%, and the correlation coefficient (R2) is 0.94.

Calibrations:

FIG. 5 shows an embodiment of a first Total THC calibration. Total THC values as measured by High Pressure Liquid Chromatography (HPLC) are on the x-axis, and Total THC values as measured by infrared spectroscopy are on the y-axis. This data set contains 129 calibration data points. Total THC values ranged from 0.1% to 33%, and the correlation coefficient (R2) is 0.94.

Note that the samples are segregated, with the high Total THC cannabis samples clustering above 5% Total THC inside the oval to the upper right in FIG. 5, whereas hemp and low Total THC cannabis samples cluster near 1% Total THC or less inside the oval in the lower left of FIG. 5. Note the significant gap between the two ovals. The dotted line denotes 5% Total THC, which in one embodiment is used as the first Total THC threshold.

Figure 6:
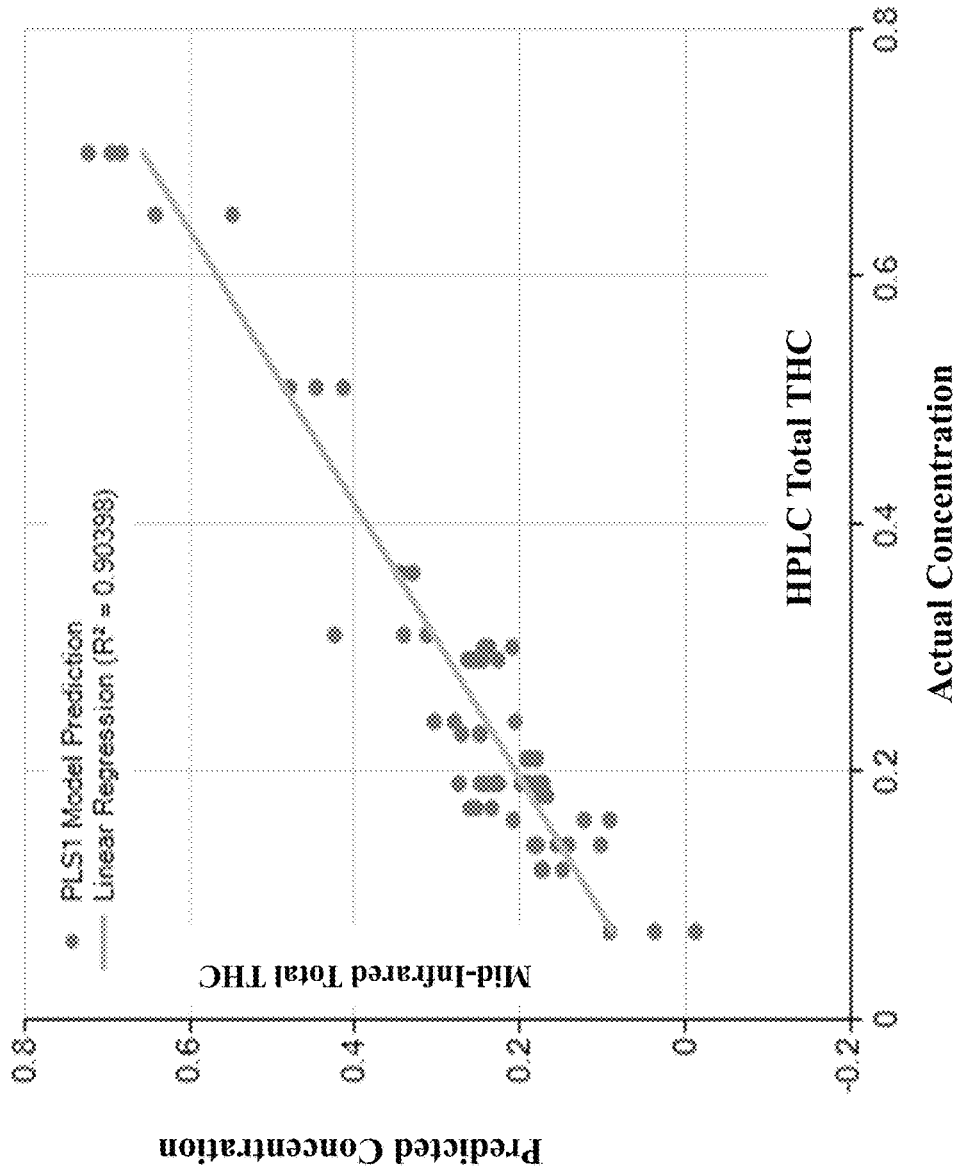
FIG. 6 The correlation chart for a low concentration Total THC calibration. Total THC values as measured by HPLC are on the x-axis, and Total THC values as measured by infrared spectroscopy are on the y-axis. This data set contains 63 calibration data points. Total THC values ranged from 0.1% to 0.7% Total THC, and the correlation coefficient (R2) is 0.9.

The global Total THC calibration models are accurate for samples with high Total THC values but are not of the desired accuracy for low Total THC samples. Again, accuracy is needed across a broad concentration range to be able to sort hemp from marijuana. Thus, a second Total THC calibration is needed to accurately measure Total THC at low concentrations. FIG. 6 shows the correlation plot for one embodiment of a second Total THC calibration model. Note it has many data points at low Total THC values. This data set contains 63 calibration data points. Total THC values ranged from 0.1% to 0.7%, and the correlation coefficient (R2) is 0.90. Calibrations like the one in FIG. 6 are of sufficient accuracy to measure Total THC in the 0.3% range accurately enough to distinguish hemp from marijuana.

Spectral Units Used:

An infrared spectrum is a plot of a property of EMR on the x-axis versus a measure of light intensity on the y-axis. In the present invention the units of the properties of light that can be used to plot the x-axis may consist of but are not limited to wavelength, wavenumber, and frequency. In one embodiment wavenumber is used. The wavenumber regions that may be used consist of but are not necessarily limited to the near infrared, the mid-infrared, and the far infrared. Examples of EMR intensity that can be plotted in spectra include but are not limited to arbitrary units, transmittance, percent transmittance, absorbance, Kubelka-Munk units, reflectance, Log reflectance, emission, scattering intensity, and emittance.

Infrared Spectrometer Types:

An infrared spectrometer is a device that measures an infrared spectrum. Amongst the spectrometer types that may be used to measure spectra for the present invention include but are not necessarily limited to grating spectrometers, Fourier transform infrared (FTIR) spectrometers, filter, tunable filter, and Fabry-Perot tunable filter spectrometers. In one embodiment a Fabry-Perot Tunable Filter Attenuated Total Reflectance spectrometer is used. It should be obvious to one of ordinary skill in the art that many other spectrometer types are possible and are covered by the present invention.

Infrared Sample Analysis Methods:

An infrared sample analysis method is a method that combines sample preparation with a way of presenting the sample to an infrared beam. The infrared sample analysis methods that may be used in the present invention consist of but are not limited to reflectance, specular reflectance, diffuse reflectance, internal reflectance, external reflectance, attenuated total reflectance, frustrated total internal reflectance, scattering, KBr pellets, mulls, cast films, and heat and pressure films. In one embodiment the attenuated total reflectance (ATR) infrared sample analysis method is used.

Calibration Types:

The present invention uses calibration models applied to infrared spectra to determine Total THC concentrations. The algorithms that may be used include but are not limited to Beer's Law, Classical Least Squares, K-Matrix, Inverse Least Squares, P-Matrix, Principal Components Analysis, Principal Components Regression, Partial Least Squares, Neural Networks, Support Vector Machine, and ANOVA.

Results:

The University of Kentucky has issued a set of 4 standard reference hemp samples. The certificates of analysis (COAs) provided with these samples are the average results of these samples analyzed by 50+ labs across the United States. The University of Kentucky sample set has been used in a validation study of how well infrared spectroscopy can quantitate Total THC in dried, ground hemp. The results are seen in Table 1.

TABLE 1

The Total THC Values for the University of Kentucky Hemp Standard Reference Materials as Determined at 50+ Labs, and as determined by mid-infrared spectroscopy.

| Sample | UKY Total THC | BSS 3000 Total THC | Diff. |
| --- | --- | --- | --- |
| September 1 | 0.29 | 0.24 | 0.05 |
| September 2 | 0.14 | 0.13 | 0.01 |
| November 1 | 0.3 | 0.22 | 0.08 |
| November 2 | 0.07 | 0.01 | 0.06 |
| | | SEPTEMBER= | 0.03 |

Note that the Standard Error of Prediction (SEP) is ±0.03 Wt. % Total. These results mean that infrared spectroscopy is accurate enough to determine if hemp is above or below the 0.3% Total THC legal limit.

The First Total THC Calibration and Challenge Sample Set Results

The job of the first Total THC calibration is to sort cannabis plant material samples into either high Total THC cannabis or low Total THC cannabis using a first Total THC calibration and a first Total THC threshold. In one embodiment the first Total THC threshold is 5%. Using this first Total THC threshold the calibration has been challenged with 491 cannabis plant material samples that are known to be above or below the first Total THC threshold. The system correctly classified 488 out of 491 samples for a success rate of 99.4%. This is very impressive given the speed, ease of use, portability, and the $0 cost per analysis of the infrared method.

The Second Total THC Calibration and Challenge Sample Set Results

If upon application of the first Total THC calibration a sample is below the first Total THC threshold, a second Total THC calibration is applied to the sample's spectrum and a second Total THC value is determined. The purpose of this calibration is to sort low THC cannabis plant material into two categories, those with a Total THC level less than the second Total THC threshold, and those with a Total THC value above the second Total THC threshold. In one embodiment the second Total THC threshold is 0.3%. In this case samples that test at or below 0.3% Total THC are legal hemp, and samples that test above this level are marijuana. A second Total THC calibration using a second Total THC threshold of 0.3% has been challenged with a set of 284 samples that are known to be either above or below 0.3% Total THC from chromatographic measurements. The calibration correctly categorized these samples as either hemp or marijuana 270 out of 284 times for a success rate of 95.1%. A summary of the results of the present invention's Total THC Classification method are seen in Table 2.

TABLE 2

Results on Challenge Samples for the
Total THC Classification Method

| Classification Type | # Classified Correctly | # of Challenge Samples | Success Rate |
|---|---|---|---|
| High Total THC marijuana vs. Low Total THC marijuana/hemp | 488 | 491 | 99.40% |
| Low Total THC marijuana vs. hemp | 270 | 284 | 95.10% |

The results in Table 2 show the Total THC Classification method when combined with the measurement of IR spectra is capable of accurately sorting cannabis plant material into the categories of marijuana and hemp.

INDUSTRIAL APPLICABILITY

As noted previously herein, there is a need in the art for accurate, fast, inexpensive, easy to use, and portable methods for distinguishing marijuana via representative sampling to enable compliance with ever-changing legal strictures. The systems and methods of the present invention meet this existing need by easily and accurately measuring Total THC in cannabis plant material and thereby discriminating between legal hemp and illegal marijuana.

While the invention has been described in detail and with reference to specific embodiments thereof, it is to be understood that the foregoing description is exemplary and explanatory in nature and is intended to illustrate the invention and its preferred embodiments. Through routine experimentation, one skilled in the art will readily recognize that various changes and modifications can be made therein without departing from the spirit and scope of the invention. Other advantages and features will become apparent from the claims filed hereafter, with the scope of such claims to be determined by their reasonable equivalents, as would be understood by those skilled in the art. Thus, the invention is intended to be defined not by the above description, but by the following claims and their equivalents.

REFERENCES

All publications mentioned herein are incorporated herein by reference in their entirety. However, nothing herein should be construed as an admission that the invention is not entitled to antedate such disclosure by virtue of prior invention.

1. Brian C. Smith, Quantitative Spectroscopy: Theory and Practice, Elsevier, Boston, 2002.
2. Brian C. Smith, Fundamentals of Fourier Transform Infrared Spectroscopy 2nd Ed., CRC Press, Boca Raton, 2011.
3. Brian C. Smith, Infrared Spectral Interpretation, A Systematic Approach, CRC Press, Boca Raton, 1999.
4. D. Burns and E. Ciurczak, eds, Handbook of Near Infrared Analysis, Marcel Dekker, New York, 1992.
5. N. Harrick, Internal Reflection Spectroscopy, Wiley, New York, 1967.
6. K. Beebe, et al., Chemometrics: A Practical Guide, Wiley, New York, 1998.
7. Douglas A Skoog, et al., Analytical Chemistry: An Introduction, 6th Edition, Saunders College Publishing: New York, N.Y., 1994.

What is claimed is:

1. A method for classifying dried, ground cannabis plant material samples, said method comprising the steps of:
   (a) measuring a spectrum or spectra of said dried, ground cannabis plant material sample using an infrared spectrometer,
   (b) applying a first Total THC calibration model to said sample spectrum or spectra measured in step (a) to determine a first Total THC value,
   (c) evaluating said first Total THC value determined in step (b) against a first Total THC threshold to classify the sample as high Total THC cannabis or low Total THC cannabis,
   (d) applying a second Total THC calibration model to said infrared spectrum or spectra of samples classified as low Total THC cannabis in step (c) to determine a second Total THC value, and
   (e) evaluating said second Total THC value obtained in step (d) against a second Total THC threshold.

2. The method of claim 1 wherein the spectral region of said infrared spectrum or spectra is chosen from the list consisting of near infrared, mid-infrared, and far infrared.

3. The method of claim 1 wherein the infrared spectrometer type is chosen from the list consisting of grating, Fourier transform, filter, tunable filter, and Fabry-Perot interferometer.

4. The method of claim 1 wherein the infrared sample analysis method is chosen from the list consisting of reflectance, specular reflectance, diffuse reflectance, internal reflectance, external reflectance, attenuated total reflectance, frustrated total internal reflectance, KBr pellets, mulls, cast films, and heat and pressure films.

5. The method of claim 1 wherein at least one of the calibration models used are chosen from the list consisting of Beer's Law, Classical Least Squares, K-Matrix, Inverse Least Squares, P-Matrix, Principal Components Analysis, Principal Components Regression, Partial Least Squares, Neural Networks, Support Vector Machine, and ANOVA.

6. A method for classifying dried, ground cannabis plant material samples, said method comprising the steps of:
   (a) measuring a mid-infrared spectrum or spectra of said cannabis plant material sample using a Fabry-Perot Interferometer-Attenuated Total Reflectance spectrometer,
   (b) applying a first Total THC calibration to said sample spectrum or spectra measured in step (a) to determine a first Total THC value,
   (c) evaluating said first Total THC value obtained in step (b) against a first Total THC threshold to classify the sample as high Total THC cannabis or low Total THC cannabis,
   (d) applying a second Total THC calibration model to said mid-infrared spectrum or spectra of a sample classified as low Total THC cannabis in step (c) to determine a second Total THC value, and (e) evaluating said second Total THC value against a second Total THC threshold, and (f) classifying said dried, ground cannabis plant material sample having said second Total THC value below said second Total THC threshold as low Total THC cannabis.

7. A method for distinguishing hemp from marijuana, said method comprising of the steps of:

(a) measuring a mid-infrared spectrum or spectra of a dried, ground cannabis plant material sample using a Fabry-Perot Interferometer-Attenuated Total Reflectance spectrometer, (b) applying a first Total THC calibration to the sample spectrum or spectra measured in step (a) to determine a first Total THC value, (c) evaluating the first Total THC value obtained in step (b) against a first Total THC threshold to classify the dried, ground cannabis plant material sample as high Total THC cannabis or low Total THC cannabis;

(d) applying a second Total THC calibration model to said mid-infrared spectrum or spectra in those samples classified as low Total THC cannabis in step (c) so as to determine a second Total THC value, and (e) evaluating the second Total THC value determined in step (d) against a second Total THC threshold, wherein a cannabis sample exhibiting a second Total THC value that falls below said second Total THC value is categorized as hemp whereas a cannabis sample exhibiting a second Total THC value is categorized as marijuana.

\* \* \* \* \*